US010156527B2

(12) United States Patent
Janik et al.

(10) Patent No.: US 10,156,527 B2
(45) Date of Patent: Dec. 18, 2018

(54) COMPACT TWO-SIDED RETICLE INSPECTION SYSTEM

(71) Applicant: ASML HOLDING N.V., Veldhoven (NL)

(72) Inventors: Stanley G. Janik, Naugatuck, CT (US); Yuli Vladimirsky, Weston, CT (US); James H. Walsh, Newtown, CT (US)

(73) Assignee: ASML Holding N.V., Veldhoven (NL)

( * ) Notice: Subject to any disclaimer, the term of this patent is extended or adjusted under 35 U.S.C. 154(b) by 0 days.

(21) Appl. No.: 15/120,154

(22) PCT Filed: Mar. 5, 2015

(86) PCT No.: PCT/EP2015/054578
§ 371 (c)(1),
(2) Date: Aug. 19, 2016

(87) PCT Pub. No.: WO2015/161949
PCT Pub. Date: Oct. 29, 2015

(65) Prior Publication Data
US 2017/0212057 A1      Jul. 27, 2017

Related U.S. Application Data

(60) Provisional application No. 61/983,753, filed on Apr. 24, 2014.

(51) Int. Cl.
*G01N 21/94* (2006.01)
*G03F 1/84* (2012.01)
(Continued)

(52) U.S. Cl.
CPC ....... *G01N 21/94* (2013.01); *G01N 21/95607* (2013.01); *G03F 1/84* (2013.01);
(Continued)

(58) Field of Classification Search
CPC ......... G01N 2021/95676; G01N 21/94; G01N 21/55; G03F 7/7085; G03F 7/70916;
(Continued)

(56) References Cited

U.S. PATENT DOCUMENTS 3,963,354 A * 6/1976 Feldman ................ G01B 11/24
                                                                   250/559.04
4,623,256 A * 11/1986 Ikenaga .................... G03F 1/84
                                                                   257/E21.211
(Continued)

FOREIGN PATENT DOCUMENTS

KR          2011/0125906 A1      11/2011

OTHER PUBLICATIONS

English-Language Abstract for Korean Patent Publication No. KR 2011/0125906, published Nov. 22, 2011; 1 page.
(Continued)

*Primary Examiner* — Deoram Persaud
(74) *Attorney, Agent, or Firm* — Sterne, Kessler, Goldstein & Fox P.L.L.C.

(57) ABSTRACT

An apparatus and method is provided to efficiently and more precisely inspect reticles for contamination. The inspection system is used to image the reticle back-side and pellicle-side separately by transferring the reticle while maintaining desired demagnification. An inspection system is disclosed that includes a reticle support to support the reticle at a first position and an illumination source to illuminate a first surface of the reticle at the first position. The inspection system further includes a first sensor to receive light from the illuminated first surface of the reticle when the reticle is at the first position and a second sensor to receive light from an illuminated second surface of the reticle when the reticle is at a second position.

13 Claims, 6 Drawing Sheets

(51) Int. Cl.
*G01N 21/956* (2006.01)
*G03F 7/20* (2006.01)

(52) U.S. Cl.
CPC .......... *G03F 7/70591* (2013.01); *G01N 2021/95676* (2013.01); *G01N 2201/062* (2013.01); *G01N 2201/0612* (2013.01); *G01N 2201/12* (2013.01)

(58) Field of Classification Search
CPC ......... H01L 2924/0002; H01L 2924/00; H01L 21/02238; H01L 21/02252; H01L 21/31116; H01L 22/12; H01L 22/26; H01L 29/6659; H01J 37/32192; H01J 37/32963; H01J 37/32972
See application file for complete search history.

(56) References Cited

U.S. PATENT DOCUMENTS

| | | | |
|---|---|---|---|
| 4,718,767 A | 1/1988 | Hazama | |
| 4,952,058 A * | 8/1990 | Noguchi | G01N 21/94 356/237.5 |
| 5,098,191 A * | 3/1992 | Noguchi | G01N 21/95607 356/237.5 |
| 5,359,407 A * | 10/1994 | Suzuki | G01N 21/8806 250/559.41 |
| 5,381,225 A * | 1/1995 | Kohno | G01N 21/94 250/559.48 |
| 5,963,316 A | 10/1999 | Miura et al. | |
| 6,064,477 A * | 5/2000 | Matsumoto | G01N 21/94 356/237.2 |
| 6,469,784 B2 * | 10/2002 | Golberg | G01N 21/94 356/237.2 |
| 8,736,688 B2 * | 5/2014 | Pichon | G01N 21/958 348/207.99 |
| 8,994,918 B2 * | 3/2015 | Sogard | G03F 1/84 355/52 |
| 9,588,421 B2 * | 3/2017 | Takehisa | G03F 1/62 |
| 2008/0259319 A1 * | 10/2008 | Mitome | G01N 21/47 356/73 |
| 2010/0045955 A1 | 2/2010 | Vladimirsky et al. | |

OTHER PUBLICATIONS

International Search Report and Written Opinion of the International Search Authority directed to related International Patent Application No. PCT/EP2015/054578, dated May 12, 2015; 9 pages.

International Preliminary Report on Patentability directed to related International Patent Application No. PCT/EP2015/054578, dated Oct. 25, 2016; 7 pages.

* cited by examiner

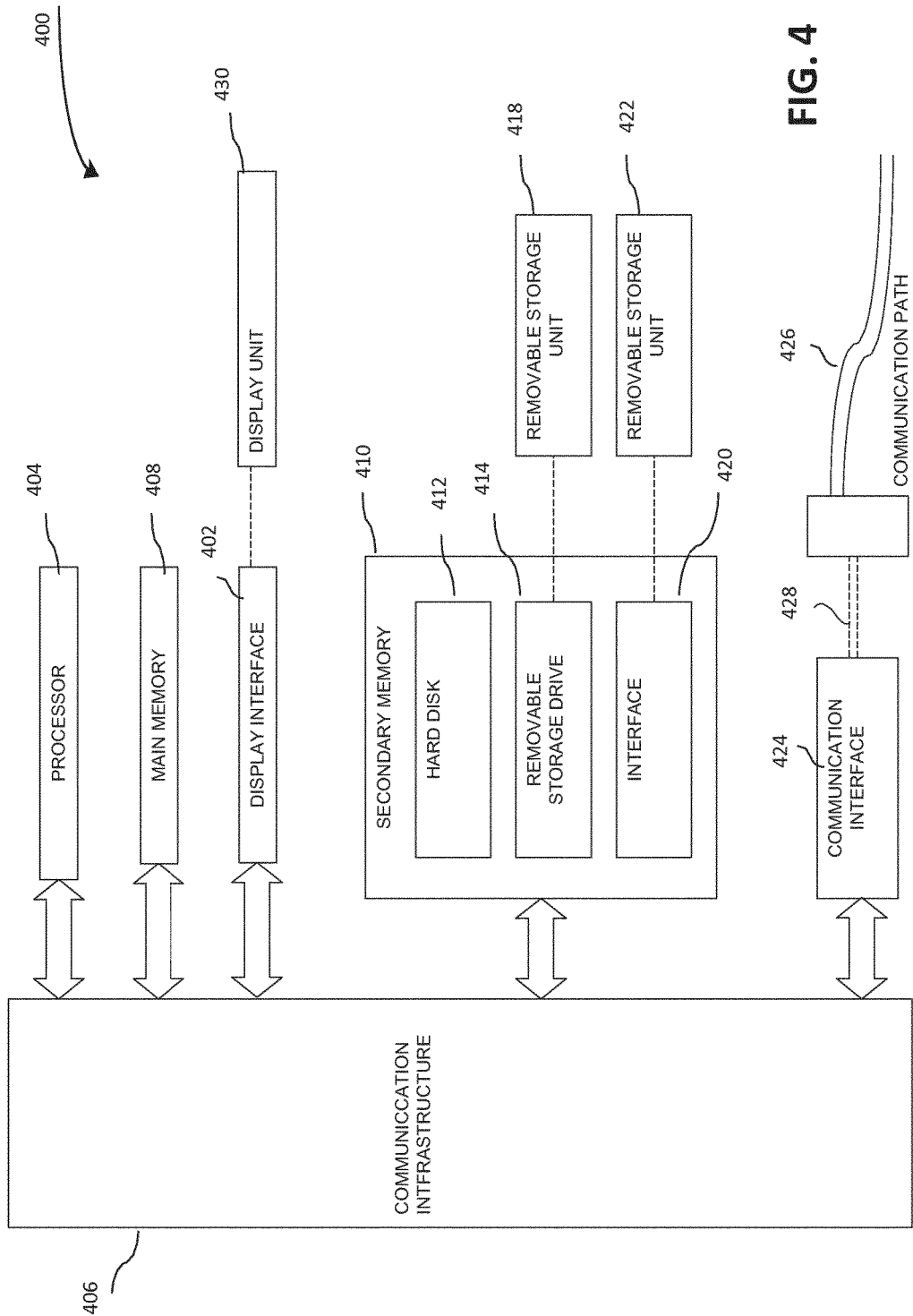

COMPACT TWO-SIDED RETICLE INSPECTION SYSTEM

CROSS-REFERENCE TO RELATED APPLICATIONS

This application is related to U.S. Patent Application No. 61/983,753, filed Apr. 24, 2014 which is incorporated by reference herein in its entirety.

FIELD

Embodiments of the present invention relate to a system and method for reticle contamination inspection.

RELATED ART

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of a die, one die, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning" direction), while synchronously scanning the substrate parallel or anti-parallel to this direction.

A lithographic apparatus typically includes an illumination system configured to condition a radiation beam, a support structure constructed to hold a patterning device, such as a reticle or mask, the patterning device being capable of imparting the radiation beam with a pattern in its cross-section to form a patterned radiation beam, a substrate table constructed to hold a substrate, and a projection system configured to project the patterned radiation beam onto a target portion of the substrate. Current lithography systems project mask pattern features that are extremely small. Dust or extraneous particulate matter appearing on the surface of the reticle can adversely affect the resulting product. Any particulate matter that deposits on the reticle before or during a lithographic process is likely to distort features in the pattern being projected onto a substrate. Therefore, the smaller the feature size, the smaller the size of particles that it is critical to eliminate from the reticle.

Lithographic reticle particulate contamination inspection systems are designed with the capability to inspect both sides of the reticle glass—back-side and front-pellicle surfaces. Large areas (for example, 6 inches×6 inches) and high optical resolution require small demagnifications, long optical paths, and bulky optical arrangement that occupy valuable space in the lithographic machines. Reticle inspection system volume minimization or compaction is achieved by multiple folding of the optical paths, still requiring separate focusing on the two surfaces intended for inspection. Use of folding elements and mirrors in the inspection system complicates the optical design, causing element positioning instabilities, excessive sensitivity to vibration (especially when moving parts are present, as in the probe-beam scanning arrangements), as well as posing difficulties in maintenance and repair. These constraints manifest in degradation of the inspection system performance, reliability, and longevity.

SUMMARY

Accordingly, there is a need for improved systems and methods for addressing the constraints with reticle contamination inspection systems.

In an embodiment, an inspection system includes a reticle support that is configured to support a reticle at a first position such that an illumination source illuminates a first surface of the reticle at the first position. The inspection system further includes a first sensor configured to receive light from the illuminated first surface of the reticle when the reticle is at the first position. The reticle support is further configured to support the reticle at a second position, and the illumination source is further configured to illuminate a second surface of the reticle at the second position. The inspection system further includes a second sensor that is configured to receive light from an illuminated second surface of the reticle when the reticle is at a second position.

According to another embodiment, there is provided a method for positioning a reticle at a first position and illuminating a first surface of the reticle at the first position. The method further includes receiving light from the illuminated first surface of the reticle when the reticle is at the first position, transferring the reticle from the first position to a second position, and illuminating a second surface of the reticle at the second position. The method further includes receiving light from an illuminated second surface of the reticle when the reticle is at a second position.

Yet another embodiment is directed to a lithography system including an inspection system, a second illumination source, and a projection system. The inspection system includes a reticle support that is configured to support a reticle at a first position and an illumination source that is configured to illuminate a first surface of the reticle at the first position. The inspection system further includes a first sensor that is configured to receive light from the illuminated first surface of the reticle when the reticle is at the first position. The reticle support is further configured to support the reticle at a second position, and the illumination source is further configured to illuminate a second surface of the reticle at the second position. The inspection system further includes a second sensor that is configured to receive light from an illuminated second surface of the reticle when the reticle is at a second position.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

FIG. 4 illustrates an example computer system that can be configured to implement features and embodiments of the present disclosure.

Figure 1A:
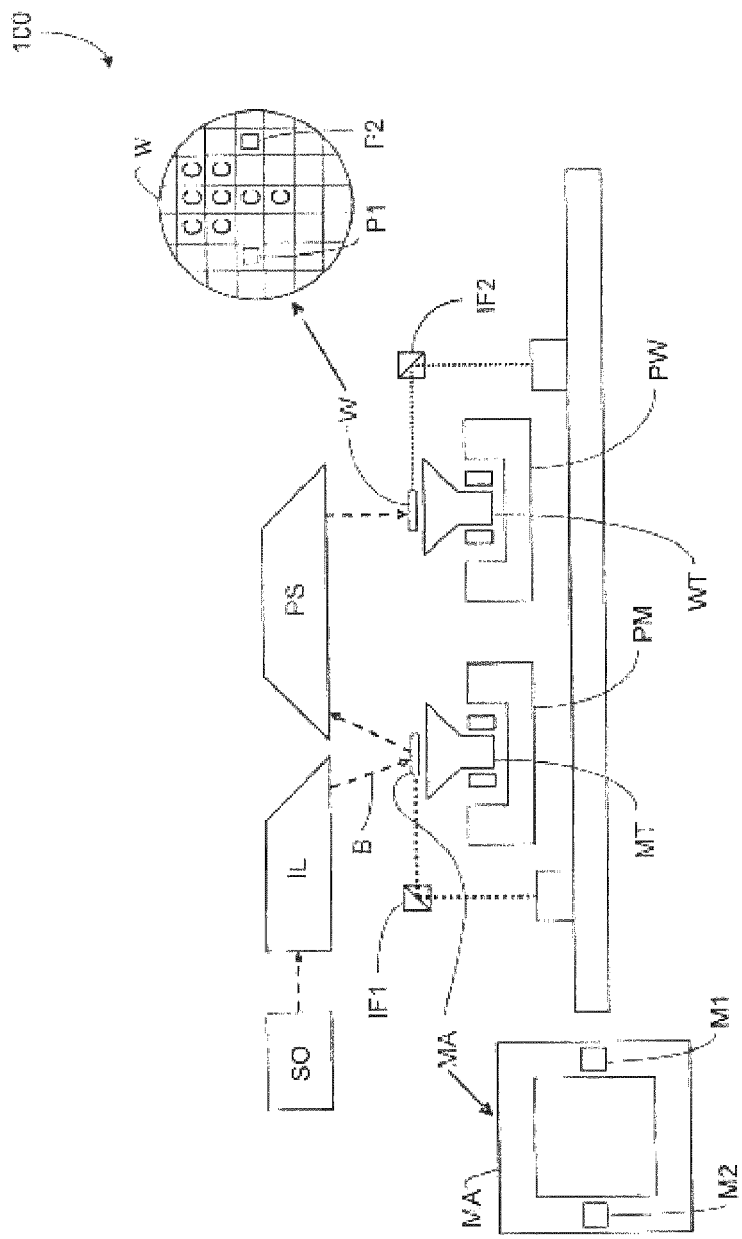
FIG. 1A is a schematic illustration of a reflective lithographic apparatus according to an embodiment.

The features and advantages of the present invention will become more apparent from the detailed description set forth below when taken in conjunction with the drawings. In the drawings, like reference numbers generally indicate identical, functionally similar, and/or structurally similar elements. Generally, the drawing in which an element first appears is typically indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Before describing such embodiments in more detail, however, it is instructive to present an example environment in which embodiments of the present invention may be implemented.

Figure 1B:
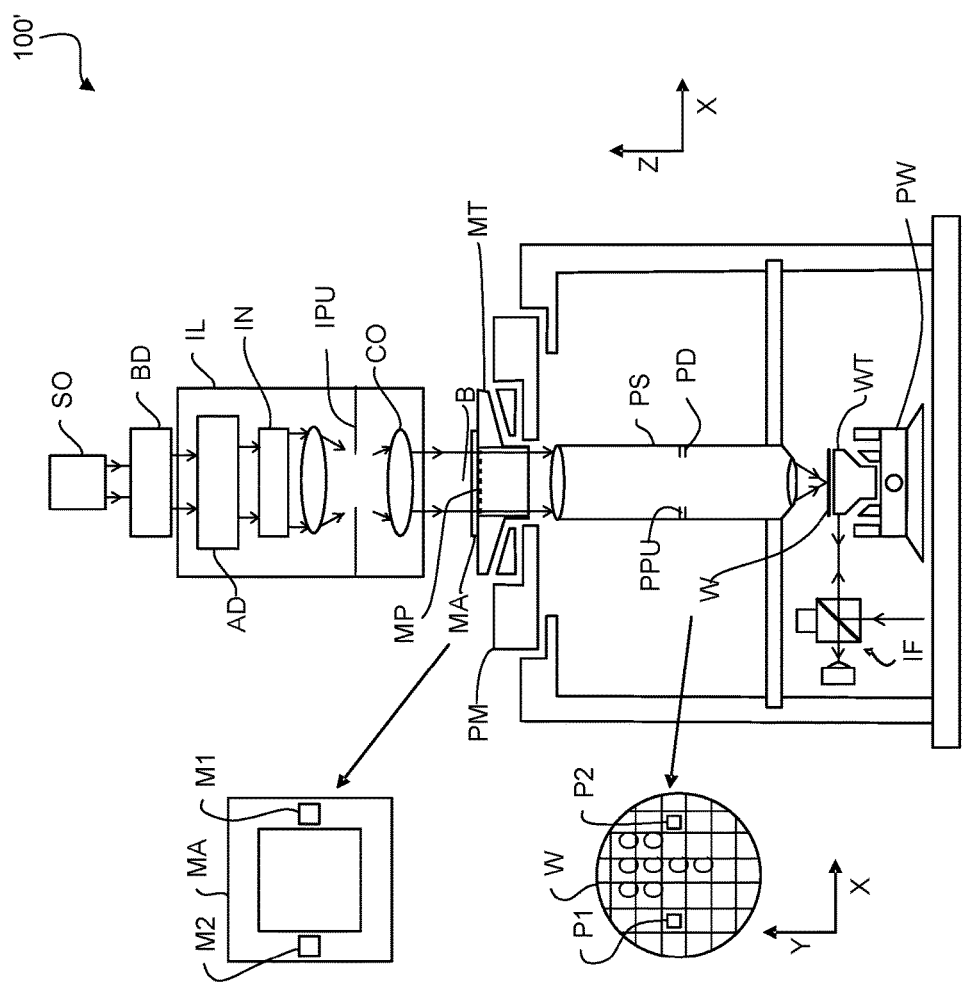
FIG. 1B is a schematic illustration of a transmissive lithographic apparatus according to an embodiment.

FIGS. 1A and 1B are schematic illustrations of a lithographic apparatus 100 and lithographic apparatus 100', respectively, in which embodiments of the present invention may be implemented. Lithographic apparatus 100 and lithographic apparatus 100' each include the following: an illumination system (illuminator) IL configured to condition a radiation beam B (for example, deep ultraviolet or extreme ultraviolet radiation); a support structure (for example, a mask table) MT configured to support a patterning device (for example, a mask, a reticle, or a dynamic patterning device) MA and connected to a first positioner PM configured to accurately position the patterning device MA; and, a substrate table (for example, a wafer table) WT configured to hold a substrate (for example, a resist-coated wafer) W and connected to a second positioner PW configured to accurately position the substrate W. Lithographic apparatus 100 and 100' also have a projection system PS configured to project a pattern imparted to the radiation beam B by patterning device MA onto a target portion (for example, comprising one or more dies) C of the substrate W. In lithographic apparatus 100, the patterning device MA and the projection system PS are reflective. In lithographic apparatus 100', the patterning device MA and the projection system PS are transmissive.

The illumination system IL may include various types of optical components, such as refractive, reflective, catadioptric, magnetic, electromagnetic, electrostatic, or other types of optical components, or any combination thereof, for directing, shaping, or controlling the radiation beam B.

The support structure MT holds the patterning device MA in a manner that depends on the orientation of the patterning device MA with respect to a reference frame, the design of at least one of the lithographic apparatus 100 and 100', and other conditions, such as whether or not the patterning device MA is held in a vacuum environment. The support structure MT may use mechanical, vacuum, electrostatic, or other clamping techniques to hold the patterning device MA. The support structure MT can be a frame or a table, for example, which can be fixed or movable, as required. By using sensors, the support structure MT can ensure that the patterning device MA is at a desired position, for example, with respect to the projection system PS.

The term "patterning device" MA should be broadly interpreted as referring to any device that can be used to impart a radiation beam B with a pattern in its cross-section, such as to create a pattern in the target portion C of the substrate W. The pattern imparted to the radiation beam B can correspond to a particular functional layer in a device being created in the target portion C to form an integrated circuit.

The patterning device MA may be transmissive (as in lithographic apparatus 100' of FIG. 1B) or reflective (as in lithographic apparatus 100 of FIG. 1A). Examples of patterning devices MA include reticles, masks, programmable mirror arrays, and programmable LCD panels. Masks are well known in lithography, and include mask types such as binary, alternating phase shift, and attenuated phase shift, as well as various hybrid mask types. An example of a programmable mirror array employs a matrix arrangement of small mirrors, each of which can be individually tilted so as to reflect an incoming radiation beam in different directions. The tilted mirrors impart a pattern in the radiation beam B which is reflected by a matrix of small mirrors.

The term "projection system" PS can encompass any type of projection system, including refractive, reflective, catadioptric, magnetic, electromagnetic and electrostatic optical systems, or any combination thereof, as appropriate for the exposure radiation being used, or for other factors, such as the use of an immersion liquid on the substrate W or the use of a vacuum. A vacuum environment can be used for EUV or electron beam radiation since other gases can absorb too much radiation or electrons. A vacuum environment can therefore be provided to the whole beam path with the aid of a vacuum wall and vacuum pumps.

Lithographic apparatus 100 and/or lithographic apparatus 100' can be of a type having two (dual stage) or more substrate tables WT (and/or two or more mask tables). In such "multiple stage" machines, the additional substrate tables WT can be used in parallel, or preparatory steps can be carried out on one or more tables while one or more other substrate tables WT are being used for exposure. In some situations, the additional table may not be a substrate table WT.

Referring to FIGS. 1A and 1B, the illuminator IL receives a radiation beam from a radiation source SO. The source SO and the lithographic apparatus 100, 100' can be separate physical entities, for example, when the source SO is an excimer laser. In such cases, the source SO is not considered to form part of the lithographic apparatus 100 or 100', and the radiation beam B passes from the source SO to the illuminator IL with the aid of a beam delivery system BD (in FIG. 1B) including, for example, suitable directing mirrors and/or a beam expander. In other cases, the source SO can be an integral part of the lithographic apparatus 100, 100'— for example when the source SO is a mercury lamp. The source SO and the illuminator IL, together with the beam delivery system BD, if required, can be referred to as a radiation system.

The illuminator IL can include an adjuster AD (in FIG. 1B) for adjusting the angular intensity distribution of the radiation beam. Generally, at least the outer and/or inner radial extent (commonly referred to as "σ-outer" and "σ-inner," respectively) of the intensity distribution in a pupil plane of the illuminator can be adjusted. In addition, the illuminator IL can comprise various other components (in FIG. 1B), such as an integrator IN and a condenser CO. The illuminator IL can be used to condition the radiation beam B to have a desired uniformity and intensity distribution in its cross section.

Referring to FIG. 1A, the radiation beam B is incident on the patterning device (for example, mask) MA, which is held on the support structure (for example, mask table) MT, and is patterned by the patterning device MA. In lithographic apparatus 100, the radiation beam B is reflected from the patterning device (for example, mask) MA. After being reflected from the patterning device (for example, mask) MA, the radiation beam B passes through the projection system PS, which focuses the radiation beam B onto a target portion C of the substrate W. With the aid of the second positioner PW and position sensor IF2 (for example, an interferometric device, linear encoder, or capacitive sensor), the substrate table WT can be moved accurately (for example, so as to position different target portions C in the path of the radiation beam B). Similarly, the first positioner PM and another position sensor IF1 can be used to accurately position the patterning device (for example, mask) MA with respect to the path of the radiation beam B. Patterning device (for example, mask) MA and substrate W can be aligned using mask alignment marks M1, M2 and substrate alignment marks P1, P2.

Referring to FIG. 1B, the radiation beam B is incident on the patterning device (for example, mask MA), which is held on the support structure (for example, mask table MT), and is patterned by the patterning device. Having traversed the mask MA, the radiation beam B passes through the projection system PS, which focuses the beam onto a target portion C of the substrate W. The projection system has a pupil PPU conjugate to an illumination system pupil IPU. Portions of radiation emanate from the intensity distribution at the illumination system pupil IPU and traverse a mask pattern without being affected by diffraction at a mask pattern and create an image of the intensity distribution at the illumination system pupil IPU.

With the aid of the second positioner PW and position sensor IF (for example, an interferometric device, linear encoder, or capacitive sensor), the substrate table WT can be moved accurately (for example, so as to position different target portions C in the path of the radiation beam B). Similarly, the first positioner PM and another position sensor (not shown in FIG. 1B) can be used to accurately position the mask MA with respect to the path of the radiation beam B (for example, after mechanical retrieval from a mask library or during a scan).

In general, movement of the mask table MT can be realized with the aid of a long-stroke module (coarse positioning) and a short-stroke module (fine positioning), which form part of the first positioner PM. Similarly, movement of the substrate table WT can be realized using a long-stroke module and a short-stroke module, which form part of the second positioner PW. In the case of a stepper (as opposed to a scanner), the mask table MT can be connected to a short-stroke actuator only or can be fixed. Mask MA and substrate W can be aligned using mask alignment marks M1, M2, and substrate alignment marks P1, P2. Although the substrate alignment marks (as illustrated) occupy dedicated target portions, they can be located in spaces between target portions (known as scribe-lane alignment marks). Similarly, in situations in which more than one die is provided on the mask MA, the mask alignment marks can be located between the dies.

Mask table MT and patterning device MA can be in a vacuum chamber, where an in-vacuum robot IVR can be used to move patterning devices such as a mask in and out of the vacuum chamber. Alternatively, when mask table MT and patterning device MA are outside of the vacuum chamber, an out-of-vacuum robot can be used for various transportation operations, similar to the in-vacuum robot IVR. Both the in-vacuum and out-of-vacuum robots need to be calibrated for a smooth transfer of any payload (e.g., mask) to a fixed kinematic mount of a transfer station.

The lithographic apparatus 100 and 100' can be used in at least one of the following modes:

1. In step mode, the support structure (for example, mask table) MT and the substrate table WT are kept essentially stationary, while an entire pattern imparted to the radiation beam B is projected onto a target portion C at one time (i.e., a single static exposure). The substrate table WT is then shifted in the X and/or Y direction so that a different target portion C can be exposed.

2. In scan mode, the support structure (for example, mask table) MT and the substrate table WT are scanned synchronously while a pattern imparted to the radiation beam B is projected onto a target portion C (i.e., a single dynamic exposure). The velocity and direction of the substrate table WT relative to the support structure (for example, mask table) MT can be determined by the (de-) magnification and image reversal characteristics of the projection system PS.

3. In another mode, the support structure (for example, mask table) MT is kept substantially stationary holding a programmable patterning device, and the substrate table WT is moved or scanned while a pattern imparted to the radiation beam B is projected onto a target portion C. A pulsed radiation source SO can be employed and the programmable patterning device is updated as required after each movement of the substrate table WT or in between successive radiation pulses during a scan. This mode of operation can be readily applied to maskless lithography that utilizes a programmable patterning device, such as a programmable mirror array.

Combinations and/or variations on the described modes of use or entirely different modes of use can also be employed.

Although specific reference can be made in this text to the use of lithographic apparatus in the manufacture of ICs, it should be understood that the lithographic apparatus described herein can have other applications, such as the manufacture of integrated optical systems, guidance and detection patterns for magnetic domain memories, flat-panel displays, liquid-crystal displays (LCDs), and thin-film magnetic heads. The skilled artisan will appreciate that, in the context of such alternative applications, any use of the terms "wafer" or "die" herein can be considered as synonymous with the more general terms "substrate" or "target portion," respectively. The substrate referred to herein can be processed, before or after exposure, in for example a track (a tool that typically applies a layer of resist to a substrate and develops the exposed resist), a metrology tool, and/or an inspection tool. Where applicable, the disclosure herein can be applied to such and other substrate processing tools. Further, the substrate can be processed more than once, for example, in order to create a multi-layer IC, so that the term substrate used herein can also refer to a substrate that already contains one or multiple processed layers.

In a further embodiment, lithographic apparatus 100 includes an extreme ultraviolet (EUV) source, which is configured to generate a beam of EUV radiation for EUV lithography. In general, the EUV source is configured in a radiation system, and a corresponding illumination system is configured to condition the EUV radiation beam of the EUV source.

In the embodiments described herein, the terms "lens" and "lens element," where the context allows, can refer to any one or combination of various types of optical components, including refractive, reflective, magnetic, electromagnetic, and electrostatic optical components.

Further, the terms "radiation" and "beam" used herein encompass all types of electromagnetic radiation, including ultraviolet (UV) radiation (for example, having a wavelength λ of 365, 248, 193, 157 or 126 nm), extreme ultraviolet (EUV or soft X-ray) radiation (for example, having a wavelength in the range of 5-20 nm such as, for example, 13.5 nm), or hard X-ray working at less than 5 nm, as well as particle beams, such as ion beams or electron beams. Generally, radiation having wavelengths between about 780-3000 nm (or larger) is considered IR radiation. UV refers to radiation with wavelengths of approximately 100-400 nm. Within lithography, the term "UV" also applies to the wavelengths that can be produced by a mercury discharge lamp: G-line 436 nm; H-line 405 nm; and/or, I-line 365 nm. Vacuum UV, or VUV (i.e., UV absorbed by gas), refers to radiation having a wavelength of approximately 100-200 nm. Deep UV (DUV) generally refers to radiation having wavelengths ranging from 126 nm to 428 nm, and in an embodiment, an excimer laser can generate DUV radiation used within a lithographic apparatus. It should be appreciated that radiation having a wavelength in the range of, for example, 5-20 nm relates to radiation with a certain wavelength band, of which at least part is in the range of 5-20 nm.

Figure 2A:
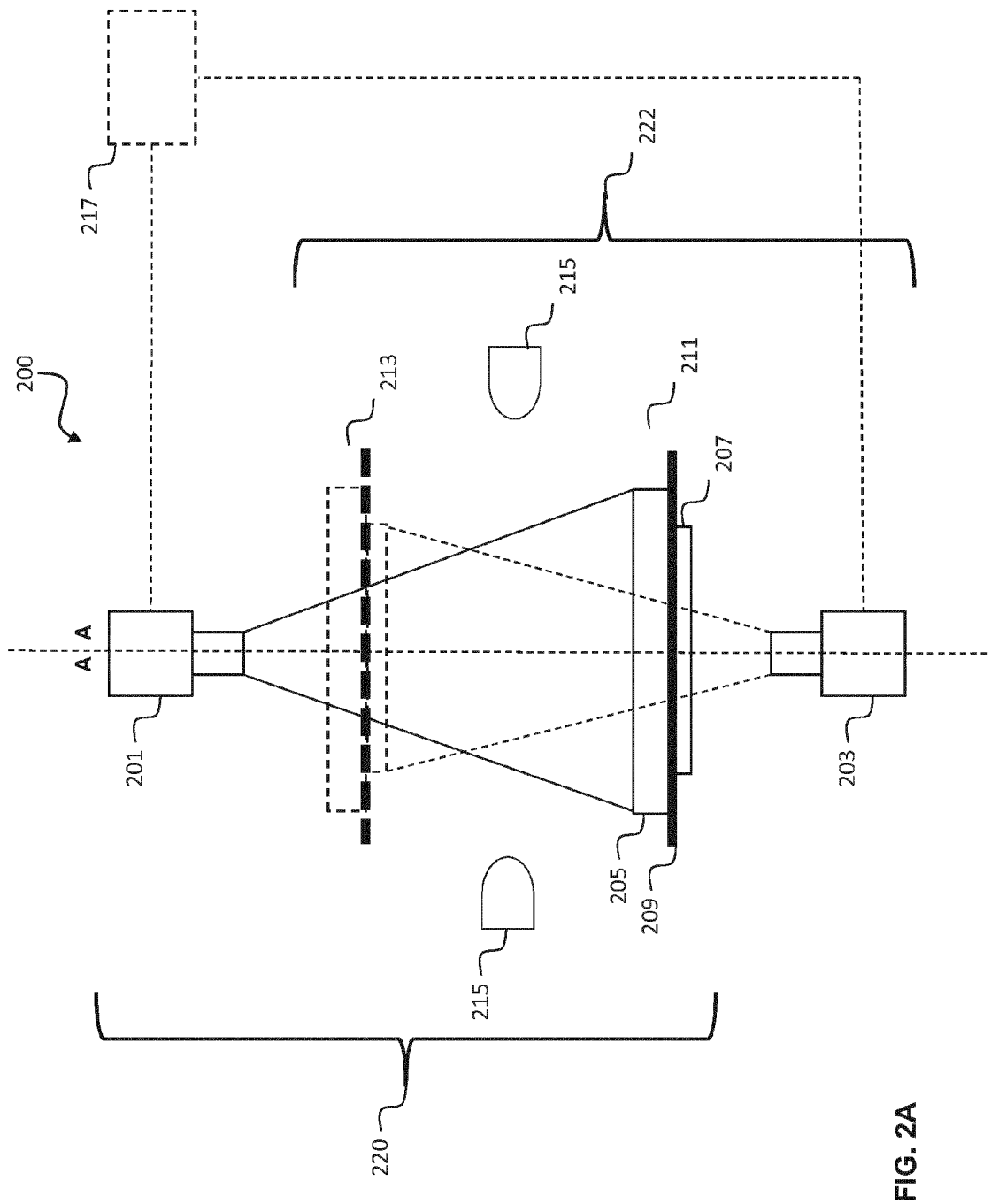
FIG. 2A is a reticle inspection system, according to an embodiment.
Figure 2B:
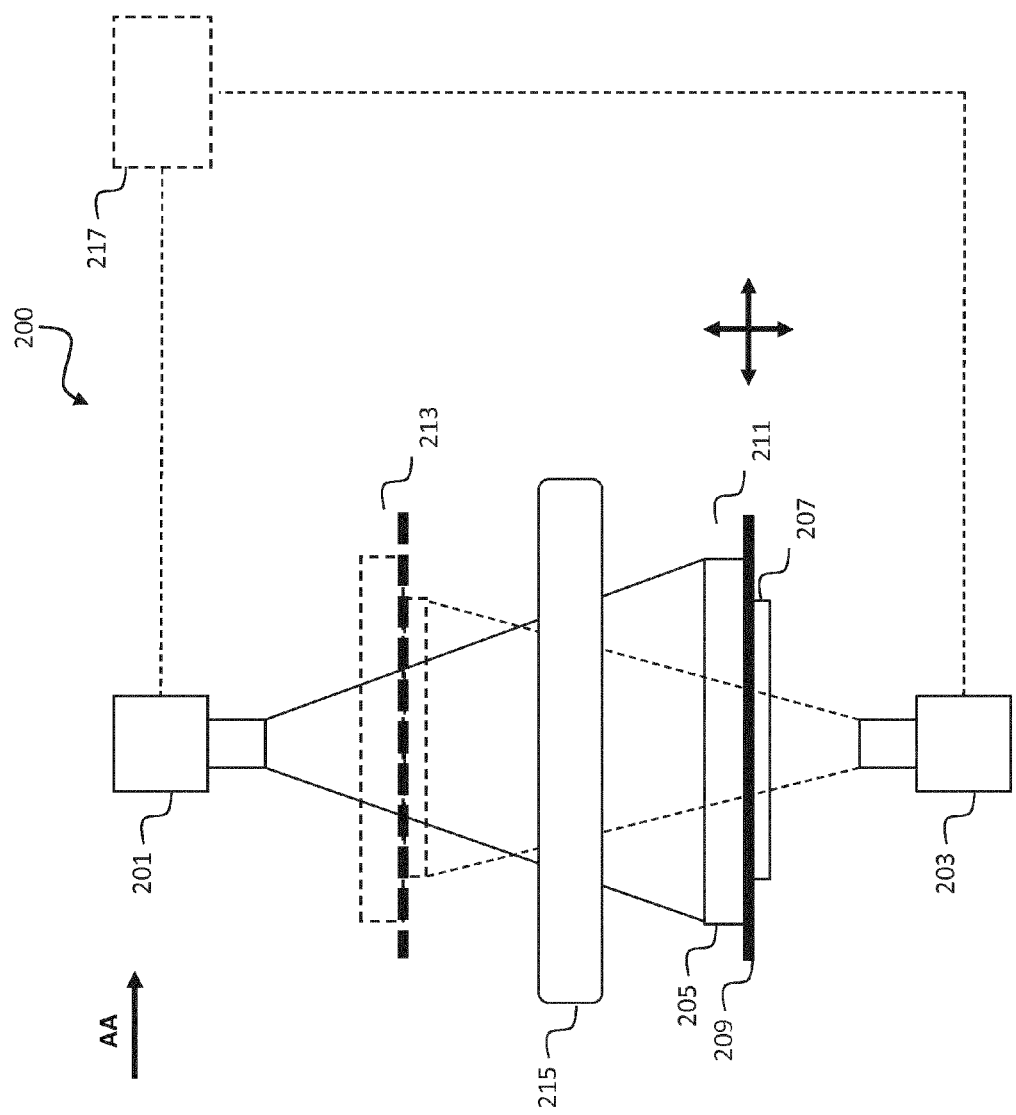
FIG. 2B is a cross-sectional view of the reticle inspection system in FIG. 2A, according to one embodiment.

FIGS. 2A and 2B illustrate a reticle inspection system, according to an embodiment. The reticle inspection system 200 can be integrated into the lithographic apparatuses of FIG. 1A and/or FIG. 1B or can be a stand-alone device. The reticle inspection system 200 includes two inspection cameras 201 and 203, a reticle support 209, and an illuminator 215. Reticle inspection system 200 can achieve efficient minimization of occupied space by over-imposing the reticle's glass back-side volume 220 and pellicle front-side imaging volume 222.

In one example, reticle support 209 can be configured to hold a reticle 205 that has a pellicle 207 attached thereto. In one embodiment, the pattern on reticle 205 (which can be used, for example, for patterning a wafer) is located on the surface of reticle 205 that is closer to pellicle 207. Pellicle 207 can be, for example, a thin transparent layer stretched over a frame above the surface of reticle 205. Pellicles are used to block particles from reaching the patterned side of a reticle surface as would become apparent to persons having ordinary skill in the lithography art. Any particles on the pellicle surface are out of the focal plane and will not form an unwanted image on the wafer being exposed. However, it is still preferable to keep the pellicle surfaces as particle-free as possible.

Reticle support 209, which in one embodiment can be (or can be attached to) a robot end-effector, is configured to support reticle 205 at two positions: position 211 and position 213. According to this example, a robot (not shown) is configured to bring reticle 205 for inspection to inspection system 200. Additionally, this robot, which can be controlled by, for example, computer system 217, is configured to move reticle support 209 (which supports reticle 205) between different positions within inspection system 200 for inspecting both sides of reticle 205. Although the embodiment of FIGS. 2A and 2B are described in accordance with a robot to transfer reticle support 209 (which supports reticle 205) between different positions, it can be understood by a person of ordinary skill in the art that other reticle positioning mechanisms can also be used to move reticle support 209 and/or reticle 205.

In one embodiment, when reticle 205 is located at position 211, one or more illuminators 215 can be configured to illuminate reticle 205 and inspection camera 201 can be configured to detect the light reflected from reticle 205. According to this example, the glass back-side of reticle 205 can be inspected using inspection camera 201 and one or more illuminators 215. In this example, inspection camera 201 can be focused on the back-side of reticle 205 (the surface closer to camera 201) to, for example, take an image of the back-side of reticle 205. In this example, camera 201 can detect contamination on this top surface. By having the depth of focus of inspection camera 201 on the back-side of reticle 205, the pattern on reticle 205 would not affect the detected image.

Additionally, when pellicle 207 (which is attached to the front-side of reticle 205) is to be inspected, the robot (not shown) can transfer reticle support 209, which supports reticle 205 and pellicle 207 to position 213. According to this embodiment, one or more illuminators 215 can be configured to illuminate pellicle 207 and inspection camera 203 can be configured to detect the light reflected from pellicle 207. According to this example, pellicle 207 can be inspected. In this example, inspection camera 203 can be focused on the bottom surface of pellicle 207 (the surface closer to camera 203) to, for example, take an image of the bottom surface of pellicle 207. In this example, camera 203 can detect contamination that could exist on this surface of pellicle 207. By having the depth of focus of inspection camera 203 on the bottom surface of pellicle 207, the pattern on reticle 205 would not affect the detected image.

According to this embodiment, two-sided inspection system 200 can use much less than double the volume of each side's focal length. Inspection system 200 can also use fewer parts in comparison to conventional inspection systems. In this embodiment, the images of reticle's glass back-side and pellicle-side are taken separately by moving reticle 205 in the proper position to retain desired demagnification. According to one embodiment, inspections system 200 can utilize one or more robots (not shown) for movements, such as for delivery, focus, etc.

Although the embodiment of FIGS. 2A and 2B are described in accordance with inspection cameras 201 and 203, it can be understood by a person of ordinary skill in the art that other detectors/sensors can also be used to detect contamination on the surface of reticle 205 and/or pellicle 207. For example, inspection camera 201 and/or 203 can include a linear or large area sensor, and can include, but is not to be limited to, a Complementary metal-oxide-semiconductor (CMOS) sensor array or a charge-coupled device (CCD). For example, inspection camera 201 and/or 203 can include a linear CCD or a large area CCD.

According to one example, one or more illuminators 215 can include an illumination source that provides illumination beams to reticle 205 and/or pellicle 207. In one example, the illumination source can be, for example, light emitting diodes (LEDs), flash light emitting diodes (flash LEDs), or laser diodes, but are not to be limited to these as other types of illumination sources can also be used. According to one example, inspection system 200 can include an optical system (not shown), which can include an optic or optics such as one or more lenses, for example, located between reticle 205 and inspection camera 201 and/or inspection camera 203. The purpose of the optical system can be to intercept scattered light from the illuminated reticle 205 and/or pellicle 207, to project a real image onto inspection camera 201 and/or inspection camera 203, and to magnify or demagnify as desired.

According to one example, inspection system 200 can include a computer system 217 that can be programmed to analyze images obtained from inspection cameras 201 and 203 to measure and/or detect any contamination on reticle 205 and/or pellicle 207. Computer system 217 can also be used to compare the detected measurements to predetermined thresholds (or other predetermined limits) in order to determine whether reticle 205 and/or pellicle 207 has contamination greater than the predetermined thresholds, and therefore stop further processes. Additionally or alternatively, computer system 217 can configure inspection cameras 201 and 203. For example, computer system 217 can be configured to change the focus depth of cameras 201 and 203. It is noted that although a separate computer system 217 is shown, all or part of the processes performed by computer system 217 can be performed by inspection cameras 201 and/or 203. Additionally or alternatively, computer system 217 can be configured to control one or more robots (not shown) to control the position of reticle support 209, e.g., to move reticle support 209 between the positions 211 and 213 for respective measurements.

Figure 3:
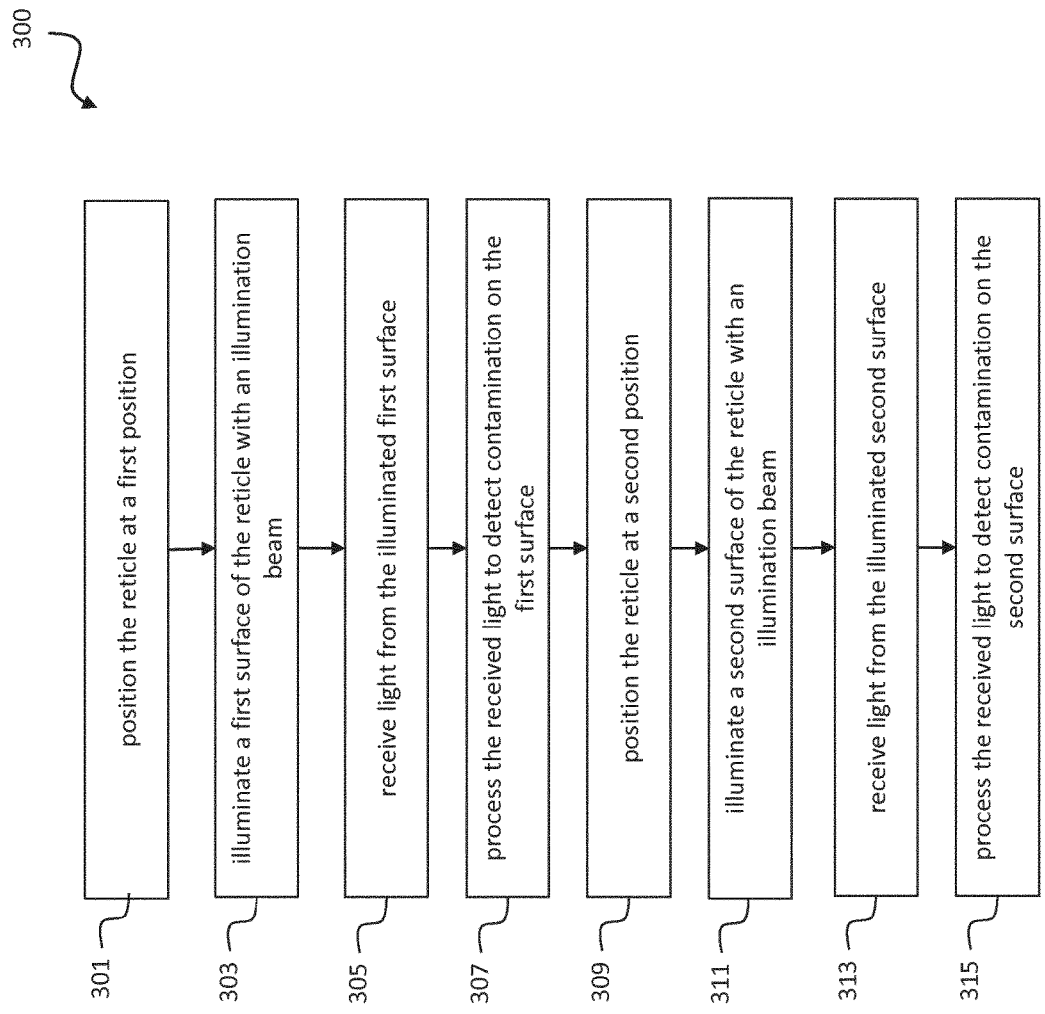
FIG. 3 is a flowchart illustrating an example method for reticle inspection, according to an embodiment.

FIG. 3 is a flowchart depicting a method 300, according to an embodiment. For example, method 300 can efficiently and more precisely detect and/or measure contamination on both sides of a reticle. In one example, method 300 is performed by inspection system 200. It is to be appreciated not all steps may be needed or performed in the order shown in FIG. 3. Reference is made to system 200 in FIGS. 2A and 2B merely for convenience of discussion. Other systems and system configurations may be used to perform the method.

In step 301, a robot (not shown) positions support 209, which supports reticle 205 (and pellicle 207 that can be attached to reticle 205), at a first position. For example, reticle 205 can be placed at position 211 such that a first surface (e.g., the glass back-side) of reticle 205 can be inspected.

In step 303, the first surface of reticle 205 is illuminated. For example, illuminator 215 can be used to illuminate the glass back-side of reticle 205, at the first position 211. At step 305, the light reflected from the first surface (e.g., the glass back-side surface of reticle 205) can be received by, for example, inspection camera/sensor 201. In step 307, the received light is processed by, for example, inspection camera 201 and/or computer system 217, to detect and/or measure contamination on the first surface.

In step 309, the robot positions support 209 (which carries reticle 205 and pellicle 207), at a second position, for example at position 213, such that the front-side (e.g., pellicle side) of the reticle can be inspected. In other words, in step 309, reticle 205 is transferred from the first position to the second position. In step 311, a second surface of reticle 205 is illuminated. For example, illuminator 215 can be used to illuminate the pellicle 207, at the second position 213. At step 313, the light reflected from the second surface can be received by, for example, inspection camera/sensor 203. In step 315, the light received from pellicle 207 is processed, by for example inspection camera 203 and/or computer system 217, to detect and/or measure contamination on the second surface.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (for example, a computing device). For example, a machine-readable medium may include read only memory (ROM); random access memory (RAM); magnetic disk storage media; optical storage media; flash memory devices, or the like. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

An example of a computer system 400 is shown in FIG. 4. Computer system 400 can also be used as computer system 217, as described above.

The computer system 400 includes one or more processors, such as processor 404. Processor 404 may be a general purpose processor (such as, a CPU) or a special purpose processor (such as, a GPU). Processor 404 is connected to a communication infrastructure 406 (e.g., a communications bus, cross-over bar, or network). Various software embodiments can be described in terms of this exemplary computer system. After reading this description, it will become apparent to a person skilled in the relevant art(s) how to implement the invention using other computer systems and/or architectures.

Computer system 400 (optionally) includes a display interface 402 that forwards graphics, text, and other data from communication infrastructure 406 (or from a frame buffer not shown) for display on display unit 430.

Computer system 400 also includes a main memory 408, preferably random access memory (RAM), and may also include a secondary memory 410. The secondary memory 410 may include, for example, a hard disk drive 412 and/or a removable storage drive 414, representing a floppy disk drive, a magnetic tape drive, an optical disk drive, etc. The removable storage drive 414 reads from and/or writes to a removable storage unit 418 in a well-known manner. Removable storage unit 418 represents a floppy disk, magnetic tape, optical disk, solid-state disk, etc. which is read by and written to by removable storage drive 414. As will be appreciated, the removable storage unit 418 includes a computer-readable storage medium having stored therein computer software and/or data.

In alternative embodiments, secondary memory 410 may include other similar devices for allowing computer programs or other instructions to be loaded into computer system 400. Such devices may include, for example, a removable storage unit 422 and an interface 420. Examples of such may include a program cartridge and cartridge interface, a removable memory chip (such as an erasable programmable read only memory (EPROM), or programmable read only memory (PROM)) and associated socket, and other removable storage units 422 and interfaces 420, which allow software and data to be transferred from the removable storage unit 422 to computer system 400.

Computer system 400 may also include a communications interface 424. Communications interface 424 allows software and data to be transferred between computer system 400 and external devices. Examples of communications interface 424 may include a modem, a network interface (such as an Ethernet card), a communications port, a Personal Computer Memory Card International Association (PCMCIA) slot and card, wireless (e.g., Wi-Fi), etc. Software and data transferred via communications interface 424 are in the form of signals 428 which may be electronic, electromagnetic, optical or other signals capable of being received by communications interface 424. These signals 428 are provided to communications interface 424 via a communications path (e.g., channel) 426. This channel 426 carries signals 428 and may be implemented using wire or cable, fiber optics, a telephone line, a cellular link, an radio frequency (RF) link and other communications channels.

In this document, the terms "computer program medium" and "computer-readable storage medium" are used to generally refer to media such as removable storage drive 414 and a hard disk installed in hard disk drive 412. These computer program products provide software to computer system 400.

Computer programs (also referred to as computer control logic) are stored in main memory 408 and/or secondary memory 410. Computer programs may also be received via communications interface 424. Such computer programs, when executed, enable the computer system 400 to perform features of the present invention, such as analyzing a surface of an object as discussed herein. In particular, the computer programs, when executed, can enable the processor 404 to perform the features of the present invention, including the implementation of the methods illustrated in FIG. 3 discussed herein. Accordingly, such computer programs represent controllers of the computer system 400.

The descriptions above are intended to be illustrative, not limiting. Thus, it will be apparent to one skilled in the art that modifications may be made to the present invention as described without departing from the scope of the claims set out below.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An inspection system, comprising:
    a reticle support configured to support a reticle at a first position;
    an illumination source configured to illuminate a first surface of the reticle when the reticle is at the first position;
    a first sensor configured to receive light from the illuminated first surface of the reticle when the reticle is at the first position;
    the reticle support further configured to support the reticle at a second position separate from the first position;
    the illumination source further configured to illuminate a second surface of the reticle when the reticle is at the second position separate from the first position;
    a second sensor configured to receive light from the illuminated second surface of the reticle when the reticle is at the second position; and
    a processor configured to control transfer of the reticle support between the first and second positions.

2. The inspection system of claim 1, wherein the processor is further configured to determine contamination of the first and second surfaces of the reticle.

3. The inspection system of claim 1, wherein the first and second sensors include inspection cameras configured to image the first and second surfaces of the reticle.

4. The inspection system of claim 1, wherein the first surface of the reticle includes a glass back-side surface of the reticle and the second surface of the reticle includes a pellicle attached to a front-side of the reticle.

5. The inspection system of claim 1, wherein the illumination source, the first sensor, and the second sensor are integrated into a lithography system for enabling the inspection system to inspect the reticle.

6. A method, comprising:
    positioning a reticle at a first position;
    illuminating a first surface of the reticle when the reticle is at the first position;
    receiving light from the illuminated first surface of the reticle when the reticle is at the first position;
    transferring the reticle from the first position to a second position separate from the first position;
    illuminating a second surface of the reticle when the reticle is at the second position separate from the first position; and receiving light from the illuminated second surface of the reticle when the reticle is at the second position.

7. The method of claim 6, wherein receiving light from the illuminated first and second surfaces includes imaging the first and second surfaces of the reticle.

8. The method of claim 6, further comprising:
determining contamination of the first and second surfaces of the reticle.

9. The method of claim 6, wherein the first surface of the reticle includes a glass back-side surface of the reticle and the second surface of the reticle includes a pellicle attached to a front-side of the reticle.

10. A lithography system, comprising:
an inspection system including:
- a reticle support configured to support a reticle at a first position,
- an illumination source configured to illuminate a first surface of the reticle when the reticle is at the first position,
- a first sensor configured to receive light from the illuminated first surface of the reticle when the reticle is at the first position,
- the reticle support further configured to support the reticle at a second position separate from the first position;
- the illumination source further configured to illuminate a second surface of the reticle when the reticle is at the second position separate from the first position; and
- a second sensor configured to receive light from the illuminated second surface of the reticle when the reticle is at the second position,
- a processor configured to control transfer of the reticle support between the first and second positions;
- a second illumination source configured to provide a light beam; and
- a projection system configured to project a patterned light beam from the reticle onto a substrate.

11. The lithography system of claim 10, wherein the processor is further configured to determine contamination of the first and second surfaces of the reticle.

12. The lithography system of claim 10, wherein the first and second sensors include inspection cameras configured to image the first and second surfaces of the reticle.

13. The lithography system of claim 10, wherein the first surface of the reticle includes a glass back-side surface of the reticle and the second surface of the reticle includes a pellicle attached to a front-side of the reticle.

* * * * *